United States Patent [19]

Sorenson

[11] Patent Number: 4,757,059

[45] Date of Patent: Jul. 12, 1988

[54] METHOD FOR TREATING CONVULSIONS AND EPILEPSY WITH ORGANIC COPPER COMPOUNDS

[75] Inventor: John R. J. Sorenson, Little Rock, Ark.

[73] Assignee: International Copper Research Association, New York, N.Y.

[21] Appl. No.: 939,219

[22] Filed: Dec. 8, 1986

Related U.S. Application Data

[60] Division of Ser. No. 640,731, Aug. 14, 1984, Pat. No. 4,670,428, which is a continuation-in-part of Ser. No. 344,309, Feb. 1, 1982, abandoned, which is a continuation of Ser. No. 154,132, May 29, 1980, abandoned.

[51] Int. Cl.$^4$ .................... A61K 31/555; A61K 31/60
[52] U.S. Cl. .................................... 514/159; 514/184; 514/186; 514/188; 514/499; 514/500
[58] Field of Search ............... 514/156, 184, 186, 188, 514/499, 500, 159

[56] References Cited

PUBLICATIONS

Journal of Neurochemistry, 1966, vol. 13, pp. 1027–1029.

*Primary Examiner*—Frederick E. Waddell
*Attorney, Agent, or Firm*—Pennie & Edmonds

[57] ABSTRACT

Copper-dependent enzymes are required for normal brain development and function. Copper deficiency can result in pathological disorders accompanied by convulsive seizures or tremors in man and animals. The present invention is directed to a method for treating convulsions or epilepsy comprising administration of a therapeutically effective amount of an organic compound of copper having anticonvulsant activity. These compounds include copper complexes of carboxylic acids, acylsalicylates, salicylates, amino acids, imines and known anticonvulsant and antiepileptic drugs.

20 Claims, 1 Drawing Sheet

METHOD FOR TREATING CONVULSIONS AND EPILEPSY WITH ORGANIC COPPER COMPOUNDS

This application is a division of application Ser. No. 640,731 filed Aug. 14, 1984, now issued as U.S. Pat. No. 4,670,428, which in turn is a continuation-in-part of application Ser. No. 344,309 filed Feb. 1, 1982, now abandoned, which in turn is a continuation of application Ser. No. 154,132 filed May 29, 1980, now abandoned.

FIELD OF THE INVENTION

The present invention relates to a method of treating convulsions, including convulsive tremors and convulsive seizures, and, in particular, epilepsy, with organic copper compounds.

BACKGROUND OF THE INVENTION

Copper is a normal component of the human brain, which contains about 370 mg of copper per gram of tissue ash. This amount of tissue copper ranks second only to that amount found in the liver, the storage organ for copper.

Normal brain development and function requires a number of copper-dependent enzymes. The following is a list of these enzymes and their role in brain function.

| Copper-Dependent Enzyme | Role in Brain Function |
| --- | --- |
| (1) Cyctochrome c oxidase | Cellular respiration |
| (2) Cerebrocuprein (cerebral superoxide dismutase) | Dismutation of superoxide anion radicals |
| (3) Tyrosinase | Conversion of tyrosine to DOPA |
| (4) Dopamine-$\beta$-hydroxylase | Conversion of dopamine to norepinephrine and epinephrine |
| (5) Lysyl oxidase | Conversion of procollagen to tropocollagen and proelastin to elastin in the vasculature |

In addition, copper-dependent processes are required for the modulation of prostaglandin syntheses, lysosomal membrane permeability, the activity of histamine, and myelinogenesis.

A variety of brain pathologic disorders accompanied by convulsive seizures are associated with abnormal copper metabolism in humans. Serum copper is elevated in epileptic patients, but brain copper levels are markedly reduced in autopsied epileptics. The elevated serum copper concentrations may indicate physiologic mobilation of copper from the liver to the brain in life but depleted stores leading to copper deficiency may account for decreased brain levels postmortem. Children with severe copper deficiency due to inadequate intake or Menkes' Syndrome, which includes depleted liver copper stores and markedly decreased brain copper levels, are known to have convulsive seizures as a constant feature of their copper deficiency. In addition, neonatal copper deficiency and the copper deficiency associated with Menkes' Syndrome are also associated with severe or terminal central nervous system disorders.

Seizures as well as neuronal and cerebral degeneration also occur in copper-deficient animals. Both quaking mice and mottled mice exhibit tremors as well as neural and central nervous system degeneration as symptoms of their genetic copper deficiency. Rats which are made copper-deficient by removing copper from their diet also exhibit convulsive tremors and central nervous system degeneration. The observation of seizures and central nervous system degeneration in association with a reduction in brain copper levels and concomitant reduction in norepinephrine and epinephrine levels which have been proposed to be seizure modulators, are consistent with known copper requirements [Jobe, P. C., A. L. Picchioni and L. Chin, *Role of Brain Norepinephrine in Audiogenic Seizure in the Rat*, J. Pharmac. Exp. Ther., 184:1-10 (1973), hereby incorporated by reference]. Further, complexing agents which produce tremors in these animals also reduce brain copper levels [Hadzovic, S., R. Kosak and P. Stern, *The Effect of Tremorigenic Substances on the Copper Content of the Rat Brain*, J. Neurochem. 3:1027-29 (1966); Price, T. R. and P. Silberfarb, *Convulsions Following Disulfiram Treatment*, Am. J. Psychiatry, 133:235 (1976), hereby incorporated by reference]. Finally, lambs born to ewes living on copper deficient pastures have a poorly developed central nervous system and exhibit tremors. On recognition, this enzootic ataxia is prevented by injecting the pregnant ewes with copper complexes [Underwood, E. J., *In: Trace Elements in Human and Animal Nutrition*, 4th Ed. Academic Press, New York, pp. 56-108 (1977), hereby incorporated by reference].

Existing antiepileptic drugs have been found to be ineffective in treating many individuals with epilepsy. This is in part due to serious side effects associated with these agents which include: intolerance, sedation, gingival hyperplasia, ataxia, nystagmus, diplopia, vertigo, psychoses, lethargy, euphoria, mydriasis, headache, hyperactivity, confusion, hallucinations, peripheral neuropathy, gastrointestinal irritation, vomiting, nausea, epigastric pain, anorexia, increased appetite, hypoglycemia, glycosuria, osteomalacia, symptoms of systemic lupus erythematosus, dermatoses, hepatic necrosis, many blood dyscrasias and lymphadenopathy [Woodbury, D. M. and E. Fingl, *The Pharmacological Basis of Therapeutics*, 5th Ed., MacMillan Pub., New York, pp. 201-225 (1975), hereby incorporated by reference]. Ataxia, anorexia [Underwood, E. J., *In: Trace Elements in Human and Animal Nutrition*, Id.], peripheral neuropathy, nystagmus, lethargy, and osteomalacia are associated with copper deficiency [Danks, D. M., *Copper Transport and Utilization in Menkes' Syndrome and in Mottled Mice*, Inorg. Persp. Biol. Med. 1: 73-100 (1977); Sorenson, J. R. J., *Therapeutic Uses of Copper, In: Copper in the Environment*, Ed. by J. O. Nriagu, John Wiley and Sons, New York, pp. 83-162 (1979); Underwood, E. J., *In: Trace Elements in Human and Animal Nutrition*, Id., hereby incorporated by reference].

SUMMARY OF THE INVENTION

The present invention seeks to overcome the problems and disadvantages of the prior art. As pointed out, supra, existing antiepileptic drugs are ineffective in treating many individuals with epilepsy because of their toxic side-effects. If drug-induced toxicities are in part caused by the removal of copper from some copper-dependent metalloprotein or metalloenzyme via complexation as a result of therapy, then these toxicities may be avoided by treatment with a copper complex of these drugs. Because copper complexes are known to have potent antiulcer activity and lack gastrointestinal irritant activity [Sorenson, J. R. J., *Copper Chelates As Possible Active Forms of the Anti-Arthritic Agents,* J. Med. Chem. 19(1): 135-147 (1976); Sorenson, J. R. J., *Copper Complexes, A Unique Class of Antiarthritic Drugs,* Prog. Med. Chem. 15: 211-260 (1978); and Walker, W. R., R. Reeves and D. J. Kay, Role of $Cu^{2+}$ and $Zn^{2+}$ in Physiological-Activity of Histamine in Mice, Search 6: 134-135 (1975), hereby incorporated by reference], it is conceivable that at least the gastrointestinal side-effects of the existing antiepileptic drugs may be circumvented by using copper complexes in therapy. If copper complexes of the antiepileptic drugs or other copper complexes have increased anticonvulsant activities and do not cause gastrointestinal irritation of the other toxicities associated with the currently used drugs they would offer more effective and less toxic therapy of convulsions and epilepsy.

Broadly, the present invention is directed to a method for treating convulsions, including convulsive tremors and convulsive seizures, and epilepsy comprising administration of a therapeutically effective amount of an organic compound of copper (in the cuprous or cupric form) having anticonvulsant and/or antiepileptic activity.

Such compounds include but are not limited to copper complexes of imines, including the following specific types of imines which possess distinctive configurations when complexed with copper: bisethyleneimine Schiff bases, salicylidene-amino acid Schiff bases and pyridoxylidene-amino acid Schiff bases.

Such compounds further include but are not limited to copper complexes of carboxylic acids. Included among these carboxylic acids are aryl carboxylic acids and also branched and unbranched aliphatic carboxylic acids, for example, those carboxylic acids with aliphatic chains of one to seven carbons in length. The aryl carboxylic acids include, but are not limited to, acylsalicylic acids and benzoic acids. When complexed with copper the carboxylic acids are called copper carboxylates.

The organic copper compounds useful in the practice of this invention also include copper complexes of amino acids. Two molecules of the same or different amino acid complex with one atom of copper to form a distinctive copper coordination compound. The twenty common amino acids as well as other less common amino acids are potentially useful.

The organic copper compounds that can be used in the invention include copper complexes of salicylic acid and substituted salicylic acids. Such salicylic acids form copper salicylates.

One of the remarkable aspects of Applicant's invention is the demonstration that copper complexes of salicylates, acylsalicylates and amino acids exhibit anticonvulsant and/or antiepileptic activity. To Applicant's knowledge, no one has ever reported that salicylates, acylsalicylates, or amino acids alone, i.e., not complexed with copper, have any anticonvulsant and/or antiepileptic. On the contrary, what is known is that salicylate and acetylsalicylate (aspirin) actually cause convulsions at high doses, making Applicant's discovery that copper complexes of these compounds have anticonvulsant activity all the more remarkable. Applicant's discovery further supports the suggestion of reduced toxicity of copper complexes of existing anticonvulsant (antiepileptic) drugs.

Also suitable for use in the practice of this invention are copper complexes of known anticonvulsant/antiepileptic compounds. Such compounds are of the following classes: hydantoins, barbiturates, desoxybarbiturates, iminostilbenes, acetylureas, succinimides, benzodiazepines, oxazolidinediones, sulfonamides and fatty acids (saturated or unsaturated) or mixtures of any of the foregoing compounds. Remarkably, it has been found that subcutaneous administration of copper complexes of certain of the known anticonvulsant drugs, specifically amobarbital, is free of side effects (hypnosis or sedation) associated with the non-copper-complexed form of the drug. The potential for elimination of side-effects associated with known anticonvulsant and antiepileptic drugs by using copper complexes thereof is a particularly important discovery.

DESCRIPTION OF THE INVENTION

Copper complexes were synthesized using reported methods [Sorenson, J. R. J., *Copper Chelates As Possible Active Forms of the Anti-Arthritic Agents,* Id.; U.S. Pat. No. 4,221,785 of Sorenson, J. R. J., hereby incorporated by reference].

The copper complexes were submitted to the National Institute of Neurological and Communicative Disorders and Stroke (NINCDS) which has an Antiepileptic Drug Development (ADD) program to screen compounds for anticonvulsant activity. Test compounds were either dissolved in 0.9% saline, or suspended in either 30% polyethylene glycol 400 in 0.9% saline or 0.2% suspending agent like polyoxyethylene glycol or Tween 80 in 0.9% saline prior to injection into male Carworth Farms #1 mice or Sprague-Dawley rats. Thus, compounds can be administered as solutions, suspensions or ointments. Unless otherwise specified, concentrations are percent by weight.

In Phase I identification of anticonvulsant activity, test compounds were given intraperitoneally (IP) at 30, 100, 300 and, in some cases, 600 milligrams per kilogram (mg/kg) of body weight and protection against Maximal Electroshock and/or Metrazol-induced seizures was determined 30 minutes, 4 hours, or later. Initial studies using the intraperitoneal route of administration demonstrated that copper complexes were effective as anticonvulsants but stimulation or depression (rotating rod toxicity) and lethality were occasionally observed at the highest doses given. Subsequently the routine protocol was modified and certain of the test compounds (see Tables, infra) re-evaluated following subcutaneous (SC) injection at periods of up to 8 hours post injection. Subcutaneous administration can be helpful in determining whether or not hypnotic activity can be distinguished from anticonvulsant activity based upon the decreased rate of absorption associated with this route of administration as opposed to the more rapid rate of absorption associated with IP administration. With this protocol none of the copper complexes so tested was found to be toxic in the rotating rod test and no deaths were observed, even at the highest doses given. In addition, some of these compounds were found to have anticonvulsant activity at doses less than 30 mg/kg and for prolonged periods of up to 6 to 8 hours post injection.

Compounds found to be effective only at 30 minutes are viewed as rapid in onset (due to rapid distribution to the central nervous system) and of short duration. Compounds that are effective only at 4 hours are viewed as slower in onset. Those compounds that are effective at both 30 minutes and 4 hours are viewed to be rapid in onset and of prolonged duration. Variability in onset and duration may be useful in the design of therapeutic regimens in which combinations of compounds are administered to a convulsant or epileptic patient.

Minimal anticonvulsant activity and the lack of toxicity were criteria required for Phase II studies, in which the time of peak anticonvulsant effect in the Maximal Electroshock and Metrazol-induced seizures, efficacy ($ED_{50}$ values for protection against the Maximal Electroshock and Metrazol-induced seizures), and lethality ($LD_{50}$ in 24 hours) were quantified. All statistics were obtained by probit analyses.

SEIZURE MODELS

Maximal Electroshock Seizure Test. Maximal electroshock seizures were elicited with a 60 cycle alternating current of 50 mA intensity (5–7 times that necessary to elicit minimal electroshock seizures) delivered for 0.2 seconds via corneal electrodes. A drop of 0.9% saline is instilled in the eye prior to application of the electrodes in order to prevent the death of the animal. Abolition of the hind limb tonic extension component of the seizure is defined as protection.

Subcutaneous Pentylenetetrazol (Metrazol) Seizure Threshold Test. Eighty-five mg/kg of pentylenetetrazol (produces seizures in greater than 97% of mice) was administered as a 0.5% solution subcutaneous in the posterior midline. The animal was observed for 30 minutes. Failure to observe even a threshold seizure (a single episode of clinic spasms of at least 5 seconds duration) is defined as protection.

Toxicity. The rotating rod was used to evaluate neurotoxicity. The animal was placed on a 1-inch diameter knurled plastic rod rotating at 6 revolutions per minute. Normal mice can remain on a rod rotating at this speed indefinitely. Neurologic toxicity is defined as the failure of the animal to remain on the rod for 1 minute and is due to either stimulation or depression of the central nervous system.

EXPERIMENTAL EXAMPLES

Copper Complexes of Acylsalicylates

The data obtained for a number of copper complexes of acylsalicylates following subcutaneous (SC) administration are presented in Table I. Cu(II) refers to the cupric form of the compound, that is, copper with a valency of +2. Structures I and II schematically depict the generic structure of an acylsalicylate copper complex (where R represents hydrogen, branched or unbranched lower alkyl, aryl, alkyl-aryl, or substituted alkyl or aryl groups; R'' represents branched or unbranched lower alkyl, aryl, halogen, or branched or unbranched lower alkyl or aryl groups substituted with halogens or oxygen-containing substituents such as hydroxy or alkoxy or nitrogen-containing substituents such as amino or nitro; and L represents solvating or other ligands capable of bonding to copper as indicated, such as water, alcohols, amines, ethers, sulfoxides and other solvents and competing ligands). The nonsolvated form of copper complexes of acylsalicylates, i.e., in the absence of L, exhibits a central binuclear configuration (as in Structure I) characteristic of nonsolvated forms of copper complexes of carboxylic acids which associate with copper atoms via their carboxyl groups in a 4:2 (carboxylic acid:copper atom) ratio. When L is present, the copper complex can exist in either the binuclear configuration of Structure I or the mononuclear configuration of Structure II depending on the affinity of L for copper.

Structure I

Structure II

TABLE I
ANTICONVULSANT ACTIVITY (PHASE I) OF SOME COPPER COMPLEXES OF ACYLSALICYLATES

| COMPLEX | % Copper | Route | Maximal Electroshock | Metrazol |
|---|---|---|---|---|
| Cu(II)$_2$(adamantylsalicylate)$_4$ | 9 | SC[1] | I[2] | A[3] at 30 and 300 mg/kg at 30 min. |
| Cu(II)$_2$(acetylsalicylate)$_4$ | 15 | SC | I | A at 100 and 300 mg/kg at 30 min. and 6 hrs.; A at 30, 100 and 300 mg/kg at 8 hrs. |
| Cu(II)(acetylsalicylate)$_2$(dimethylsulfoxide)$_2$ | 11 | SC | I | A at 300 mg/kg at 30 min.; A at 100 mg/kg at 4 hrs. |
| Cu(II)(acetylsalicylate)$_2$(pyridine)$_2$ | 11 | SC | I | A at 300 mg/kg at 30 min.; A at 100 and 300 mg/kg at 4 hrs. |
| Cu(II)$_2$(3,5-dibromoacetylsalicylate)$_4$ | 8.6 | IP | A at 100 mg/kg at 4 hrs. | A at 100 mg/kg at 30 min. |
|  |  | SC | A at 300 mg/kg at 4 hrs. | I |
| Cu(II)$_2$(3,5-diiodoacetylsalicylate)$_4$ | 6.8 | IP | I | A at 100 mg/kg at |

TABLE I-continued

ANTICONVULSANT ACTIVITY (PHASE I)
OF SOME COPPER COMPLEXES OF ACYLSALICYLATES

| COMPLEX | % Copper | Route | Maximal Electro-shock | Metrazol |
|---|---|---|---|---|
| $(H_2O)_6$ | | | | 30 min. and 4 hrs. |
| | | SC | A at 300 mg/kg at 4 hrs. | A at 300 mg/kg at 4 hrs. |
| | | $SC^4$ | Not tested | A at 105 mg/kg at 30 min. |

[1]SC = Subcutaneous.
[2]Inactive at doses studied.
[3]Activity at doses and times indicated.
[4]Phase II data.

$Cu(II)_2$(adamantylsalicylate)$_4$ was found to have anticonvulsant activity at 30 minutes following subcutaneous injection at 30 and 300 mg/kg. $Cu(II)_2$ (acetylsalicylate)$_4$ [alternatively called copper aspirinate or $Cu(II)_2$(aspirinate)$_4$] was found to have activity at 30 minutes, 6 hours and 8 hours following subcutaneous injection of the entire range of doses studied. The dimethylsulfoxide and pyridine solvates of Cu(II)(acetylsalicylate)$_2$ were found to be effective at the higher doses studied at 30 minutes and 4 hours. None of these complexes was found to have rotating rod toxicity at any of the doses or times studied following subcutaneous injection. $Cu(II)_2$(3,5-dibromoacetylsalicylate)$_4$ and $Cu(II)_2$(3,5-diiodoacetylsalicylate)$_4$ were also effective in protecting against both models of seizure.

COPPER COMPLEXES OF SALICYLATES

Structure III

Structure IV

A group of copper complexes of salicylates with the generic structures shown schematically by structures III and IV (where R" and L represent the same groups, substituents, and ligands described for Structures I and II) were also evaluated for their anticonvulsant activity. The nonsolvated form of copper complexes of salicylates, i.e., in the absence of L, exhibits a mononuclear configuration as in Structure III. When L is present, the copper complex can exist in either the mononuclear configuration of Structure III or the binuclear configuration of Structure IV depending on the affinity of L for copper.

As shown in Table II, Cu(II)(salicylate$_2$), Cu(II)(4-tertiarybutylsalicylate)$_2$ and Cu(II)(3,5-ditertiarybutylsalicylate)$_2$ were found to be effective at the higher doses studied and for prolonged periods of up to 4 hours. Cu(II)(salicylate)$_2$(pyridine)$_2$ had activity representative of a compound with rapid onset. The 3,5-diisopropylsalicylate, 3,5-ditertiarybutylsalicylate, 3,5-dibromosalicylate and 3,5-dichlorosalicylate complexes are of special interest because they were effective in preventing both the Maximal Electroshock and Metrazol-induced seizures in Phase I studies. All of these complexes were also found to be free of rotating rod toxicity at all of the doses and time periods studied following subcutaneous injection. Also presented in Table II are data obtained for three 4-substituted salicylates, Cu(II)(4-nitro-salicylate)$_2$, Cu(II)(4-aminosalicylate)$_2$ and Cu(II)(4-acetylaminosalicylate)$_2$, which were also effective in preventing seizures. However, administration of Cu(II)(4-nitrosalicylate)$_2$ at 100 mg/kg, Cu(II)(4-aminosalicylate)$_2$ at 300 mg/kg and Cu(II)(acetylaminosalicylate)$_2$ at 600 mg/kg elicited rotating rod toxicity. Moreover, administration of Cu-(II)(4-nitrosalicylate)$_2$ at doses higher than 100 mg/kg and Cu(II)(4-aminosalicylate)$_2$ at doses higher than 300 mg/kg caused death in some of the tests groups. These deaths may have resulted from a hypnotic overdose.

TABLE II

ANTICONVULSANT ACTIVITY (PHASE I)
OF SOME COPPER COMPLEXES OF SALICYLATES

| COMPLEX | % Copper | Route | Maximal Electro-shock | Metrazol |
|---|---|---|---|---|
| Cu(II)(salicylate)$_2$ | 19 | $SC^1$ | $I^2$ | $A^3$ at 30, 100 and 300 mg/kg at 30 min.; A at 300 mg/kg at 4 hrs. |
| Cu(II)(salicylate)$_2$ (pyridine)$_2$ | — | IP | I | A at 300 mg/kg at 30 min. |
| Cu(II)$_2$ (4-tertiarybutyl-salicylate)$_2$·½H$_2$O | 14 | SC | I | A at 300 mg/kg at 30 min.; A at 300 and 600 mg/kg at 4 hrs. |
| Cu(II)(3,5-diisopropylsalicylate)$_2$ | 13 | SC | A at 300 mg/kg at 4 hrs; A at 100 and 300 mg/kg at 6 hrs.; A at 300 mg/kg at 8 hrs. | A at 30, 100 and 300 mg/kg at 30 min.; A at 100 and 300 mg/kg at 4 hrs.; A at 100 mg/kg at 6 hrs.; A at 100 and 300 mg/kg at 8 hrs. |
| Cu(II)(3,5-ditertiary-butylsalicylate)$_2$ | — | IP | A a 100 mg/kg at 4 hrs. | A at 30 and 100 mg/kg at 30 min. |
| | | SC | A at 300 mg/kg at 4 hrs. | A at 300 mg/kg at 4 hrs. |
| Cu(II) (4-nitrosalicylate)$_2$ | — | $IP^4$ | I | A at $100^3$ mg/kg$^6$ at 30 min. |
| Cu(II) | — | IP | I | A at 30, |

TABLE II-continued

ANTICONVULSANT ACTIVITY (PHASE I) OF SOME COPPER COMPLEXES OF SALICYLATES

| COMPLEX | % Copper | Route | Maximal Electro-shock | Metrazol |
|---|---|---|---|---|
| (4-aminosalicylate)$_2$ | | | | 100 and 300[5] mg/kg[6] at 30 min.; A at 100 mg/kg[6] at 4 hrs. |
| Cu(II)(4-acetyl-aminosalicylate)$_2$ | — | IP | A at 600[5] mg/kg at 30 min. | I[7] |
| Cu(II)(5-chloro-salicylate)$_2$ | — | IP | I | A at 300 mg/kg at 30 min. and 30 mg/kg at 4 hrs. |
| | | IP[8] | Not tested | A at 30 mg/kg at 6 hrs. |
| Cu(II)(3,5-dibromo-salicylate)$_2$(H$_2$O)$_3$ | — | IP | A at 300 mg/kg at 4 hrs. | A at 30 mg/kg at 30 min. and 100 mg/kg at 4 hrs. |
| | | SC | A at 300 mg/kg at 4 hrs. | A at 600 mg/kg at 4 hrs. |
| Cu(II)(3,5-dichloro-salicylate)$_2$(H$_2$O)$_2$ | — | IP | A at 600 mg/kg at 4 hrs. | A at 100 mg/kg at 30 min. |
| | | SC | I | A at 600 mg/kg at 4 hrs. |

[1]SC = Subcutaneous.
[2]Inactive at doses studied.
[3]Activity at doses and times indicated.
[4]IP = Intraperitoneal.
[5]Rotating Rod toxicity.
[6]Lethal at higher doses.
[7]Lethal at 100 mg/kg at 4 hours.
[8]Phase II data.

PHASE II EVALUATION OF Cu(II)(SALICYLATE)$_2$

The Phase I test data presented in Tables I, II (supra) and III (infra) were all obtained in a standardized protocol using routine doses and routine times for the qualitative evaluation of anticonvulsant effects of the compounds tested. The NINCDS-ADD Program Phase II follow-up evaluation of active compounds with low toxicity is a quantitation of the anticonvulsant activity and acute toxicity. The anticonvulsant activity is quantitated by determining the times of peak activity and ED$_{50}$ values in the Maximal Electroshock and Metrazol-induced seizures. The acute toxicity is quantitated by determining the 24-hour LD$_{50}$ value.

Figure 1:
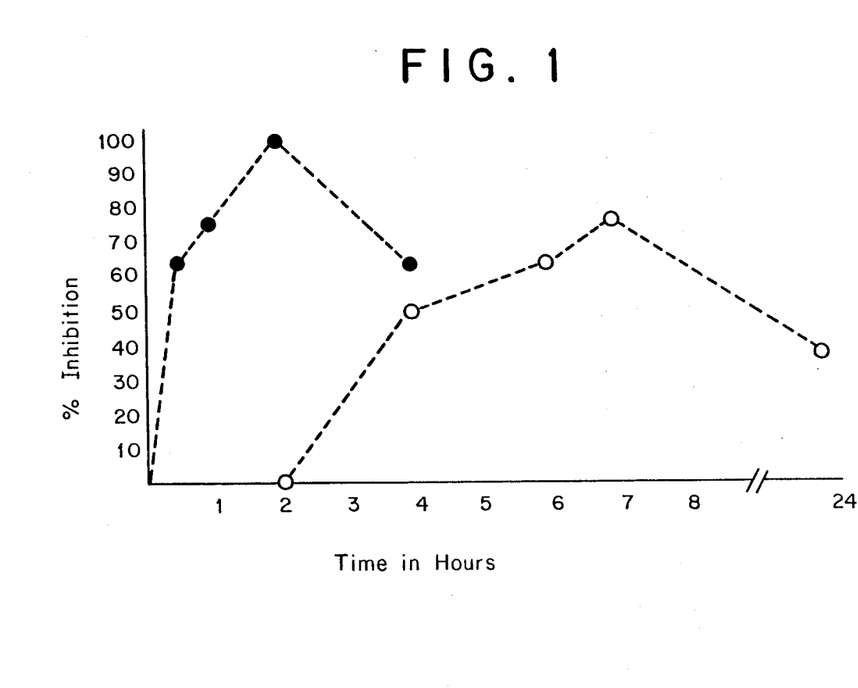
FIG. 1 graphically depicts the anticonvulsant activity versus time for $Cu(II)(salicylate)_2$ in preventing the Metrazol-induced seizure after giving 100 mg/kg subcutaneously (closed circles) and in preventing the Maximal Electroshock-induced seizure after giving 600 mg/kg subcutaneously (open circles).

The first copper complex selected by the ADD Program for Phase II evaluation was Cu(II)(salicylate)$_2$. The data presented in FIG. 1 show that the time of peak effect for the inhibition of Metrazol-induced seizures following subcutaneous administration of 100 mg/kg was 2 hours and the time of peak effect for the inhibition of Maximal Electroshock induced seizures was 7 hours following subcutaneous administration of 600 mg/kg.

These data point out that the times of peak effects were different from the time of routine evaluation in the Phase I tests and that the dose required to protect against the Maximal Electroshock-induced seizure was larger than the largest dose used in the routine Phase I test. The data plotted in FIG. I also show that there was a rapid onset of protection against the Metrazol-induced seizure which decreases over the extrapolated period of 7 hours. The onset of protection against Maximal Electroshock-induced seizure was slower but the activity was prolonged over the 24-hour period (37% inhibition at 24 hours) and beyond. The ED$_{50}$ values for protection against Maximal Electroshock and Metrazol-induced seizures were 360 mg/kg and 38 mg/kg, respectively. The LD$_{50}$ value for this compound was 441 mg/kg. This value was not much different from the ED$_{50}$ for protection against Maximal Electroshock-induced seizures but it was over 10 times the ED$_{50}$ for the prevention Metrazol-induced seizures.

These data show that while Cu(II)(salicylate)$_2$ was inactive in protecting against the Maximal Electroshock-induced seizure in routine Phase I studies, it was found to be active in protecting against this seizure when higher doses were used and the activity was evaluated at different time periods. As a result, inactivity in Phase I studies cannot be taken as evidence of no activity at any time period or higher doses. The possibility exists that these apparently inactive compounds may be active in protecting against seizures when the treatment protocol is modified to include prolonged pretreatment (i.e., longer periods of time after administration of a copper complex but before inducement of the seizure) and/or higher doses.

COPPER COMPLEXES OF AMINO ACIDS

A series of copper complexes of bidentate amino acids generically depicted by Structure V (where R represents the alpha substituents of the D or L amino acids, wherein D and L represent the configuration of the alpha carbon and where two of the same or two different amino acids form the complex and L represents solvating or other ligands such as water, alcohols, amines, ethers, sulfoxides and other solvents and competing ligands) and a copper complex of a tridentate amino acid (glutamic acid) were evaluated as anticonvulsants. The results are presented in Table III.

Structure V

TABLE III

ANTICONVULSANT ACTIVITY (PHASE I) OF SOME COPPER COMPLEXES OF AMINO ACIDS

| COMPLEX | % Copper | Route | Maximal Electro-shock | Metrazol |
|---|---|---|---|---|
| Cu(II) (L-threoninate) (L-serinate) | 22 | IP[1] | NT[2] | A[3] at 30,100 and 300 mg/kg at 30 min. and 4 hrs. |
| Cu(II) (L-threoninate) (L-alaninate) | 24 | IP | NT | A at 30, 100 and 300 mg/kg at 30 min. and 4 hrs. |

TABLE III-continued

ANTICONVULSANT ACTIVITY (PHASE I)
OF SOME COPPER COMPLEXES OF AMINO ACIDS

| COMPLEX | % Copper | Route | Maximal Electroshock | Metrazol |
|---|---|---|---|---|
| Cu(II)(L-valinate)$_2$H$_2$O | 20 | IP | NT | A at 30, 100 and 300 mg/kg at 30 min. and 4 hrs. |
| Cu(II)(L-threoninate)$_2$H$_2$O | 20 | IP | NT | A at 30, 100 and 300 mg/kg at 30 min. and 4 hrs. |
| Cu(II)(L-leucinate)$_2$ | — | SC IP | I I | I A at 100 mg/kg at 30 min. and A at 30 and 100 mg/kg at 4 hrs. |
| Cu(II)(L-isoleucinate)$_2$ | — | SC | I | A at 300 and 600 mg/kg at 30 min. and 600 mg/kg at 4 hrs. |
| Cu(II)(L-isoleucinate)$_2$ | | IP | A at 600[6] mg/kg at 30 min. | A at 100[6] mg/kg at 30 min. |

[1]Not Tested.
[2]Active at doses and times indicated.
[3]Rotating rod toxicity observed with 300 mg/kg at 4 hrs.
[4]Inactive at 30, 100, 300 and 600 milligrams per kilogram at 30 min. and 4 hrs.
[5]Rotating rod toxicity.
[6]Lethal at higher doses.

Cu(II)(L-threoninate) (L-serinate), Cu(II)(L-threoninate) (L-alaninate), Cu(II)(L-valinate)$_2$, Cu(II)(L-threoninate)$_2$ and Cu(II)(L-alaninate)$_2$ were found to be effective against the Metrazol-induced seizure at all doses studied and at both time intervals, 30 minutes and 4 hours. Rotating rod toxicity was observed with the first four of these compounds but only at the highest dose studied (300 mg/kg) at the end of the 4-hour observation. Cu(II)(L-phenylalaninate)$_2$ and Cu(II)(L-cystinate)$_2$ were also effective against the Metrazol-induced seizure at all three doses studied but only at the shorter time period.

Cu(II)(L-serinate)$_2$, Cu(II)(L-tryptophanate)$_2$, Cu-(II)(L-glutamate)$_2$, Cu(II)(L-leucinate)$_2$ and Cu(II)(L-isoleucinate)$_2$ have also been found to have anticonvulsant activity. In all cases these compounds were found to be more effective following IP than SC administration but they were also more toxic following IP administration. This is consistent with a more rapid absorption of greater amounts of these compounds following IP administration. The lethality associated with higher doses of some of the compounds is consistent with the possibility that these animals had been given hypnotic overdoses. The isoleucine complex was unique because it inhibited both the Maximal Electroshock and Metrazol-induced seizures in these Phase I tests.

COPPER COMPLEXES OF IMINES

Copper complexes of imines were evaluated for their anticonvulsant activity. The types of imine compounds tested included copper complexes of the following: (a) salicylidene-amino acid Schiff bases, the generic structure of which is depicted by Structure VI (where R represents the alpha substituents of the D or L amino acids, D and L denoting the configuration of the alpha carbon; R" represents branched or unbranched lower alkyl, aryl or halogen groups, or branched or unbranched lower alkyl or aryl groups substituted with halogens, oxygen-containing groups, e.g., hydroxy or alkoxy, or nitrogen-containing groups, e.g., amino or nitro; and L represents solvating or other ligands capable of bonding to copper as indicated, such as water, alcohols, amines, ethers, sulfoxides, and other solvents and competing ligands); (b) bisethyleneimine Schiff bases, the generic structures of which are depicted by Structures VII and VIII (where R and R" represent branched or unbranched lower alkyl, aryl or halogen groups, or branched or unbranched lower alkyl or aryl groups substituted with halogens, oxygen-containing groups, e.g., hydroxy or alkoxy, or nitrogen-containing groups, e.g., amino or nitro; and L represents solvating or other ligands capable of bonding with copper as indicated such as water, alcohols, amines, ethers, sulfoxides, and other solvents and competing ligands); and (c) pyridoxylidene-amino acid Schiff bases, the generic structure of which is depicted by Structure IX (where R represents the alpha substituents of the D or L amino acids; D and L denoting the configuration of the alpha carbon; and L represents solvating or other ligands capable of bonding with copper as indicated such as water, alcohols, amines, ethers, sulfoxides, and other solvents and competing ligands).

Structure VI

Structure VII

Structure VIII

Structure IX

TABLE IV

ANTICONVULSANT ACTIVITY (PHASE I) OF SOME COPPER COMPLEXES OF SALICYLIDENE-AMINO ACID AND BISETHYLENEIMINE SCHIFF BASES

| COMPLEX | Route | Maximal Electroshock | Metrazol |
|---|---|---|---|
| Cu(II) Salicylidene-L-valinate | SC | I | A (slight) at 100 and 300 mg/kg[2] at 4 hrs. |
| | IP | I | A at 100 mg/kg[2] at 30 min. and 30 mg/kg[2] at 4 hrs. |
| Cu(II) Salicylidene-L-histidinate | SC | I | A (slight) at 600 mg/kg at 30 min. |
| | IP | I | I |
| Cu(II) Bisacetylacetonethyleneimine | SC | A at 100 mg/kg at 30 min.; A at 100, 300' and 600' at 4 hrs. | A at 100, 300' and 600' mg/kg at 4 hrs. |
| Cu(II) bissalicylato-ethyleneimine | SC | I | I |
| | IP | I | A (marginal) at 300 and 600 mg/kg at 4 hrs. |

A = Active.
I = Inactive at doses studied.
IP = Intraperitoneal.
SC = Subcutaneous.
[1]Rotating rod toxicity.
[2]Lethal at higher doses.

The data obtained with copper complexes of salicylidene-amino acid Schiff bases and bisethyleneimine Schiff bases are presented in Table IV. The majority of these copper complexes had weak activity. The salicylidene-L-valinate complex also caused lethality at higher doses. The bisacetylacetonethyleneimine complex was effective in preventing both Maximal Electroshock and Metrazol-induced seizures, but rotating rod toxicity, which may also have been due to hypnotic activity, was found at the higher doses studied.

The data obtained with copper complexes of pyridoxylidene-amino acid Schiff bases are presented in Table V. These data show that the pyridoxylideneglycinate complex protected against both types of seizure. The serinate, tryptophanate and threoninate complexes were more effective but only protected against the Metrazol-induced seizure. The phenylalaninate and valinate complexes had no activity.

Some of these complexes are as active or more active than existing antiepileptic drugs. Other potentially useful copper complexes of pyridoxylideneamino acid Schiff bases include complexes of the following: tyrosine, dihydroxyphenylalanine (DOPA), 5-hydroxytryptophan, glutamic acid, gamma aminobutyric acid, aspartic acid, and beta-alanine.

TABLE V

PHASE I ANTICONVULSANT DATA OF PYRIDOXYLIDENEAMINOACID COPPER COMPLEXES

| Complex | Route | Challenge Time | Seizure Model[1] MES | Metrazol |
|---|---|---|---|---|
| Cu(II)Pyridoxylidene-glycinate(H2O)1.5 | IP | 30 min | 300 | 100 |
| | | 4 hrs | I | I |
| Cu(II)Pyridoxylidene-L-serinate(H2O) | IP | 30 min | I | 100 |
| | | 4 hrs | I | 100 |
| Cu(II)Pyridoxylidene-L-tryptophanate(H2O)2 | IP | 30 min | I | 30 |
| | | 4 hrs | I | 30 |
| Cu(II)Pyridoxylidene-L-threoninate(H2O)2 | IP | 30 min | I | 30 |
| | | 4 hrs | I | 30 |
| Cu(II)Pyridoxylidene-L-phenylalaninate(H2O)2 | IP | 30 min | I | I |
| | | 4 hrs | I | I |
| Cu(II)Pyridoxylidene-L-valinate(H2O) | IP | 30 min | I | I |
| | | 4 hrs | I | I |

[1]The numerical values are the lowest active doses in mg/kg of body weight; I = Inactive; MES = Maximal Electroshock.

COPPER COMPLEXES OF CARBOXYLIC ACIDS

Several copper complexes of carboxylic acids have been tested for their anticonvulsant activity. The carboxylic acids include branched and straight chain aliphatic carboxylic acids as well as aryl carboxylic acids. In their nonsolvated state (i.e., in the absence of L), such carboxylic acids form a characteristic binuclear complex of copper as schematically depicted by Structure X (where R represents alkyl, aryl, aryl-alkyl groups wherein substituents may be hydrogen, halogen, oxygen-containing, e.g., hydroxy or alkoxy, or nitrogen-containing, e.g., amino or nitro substituents; and L represents solvating or other ligands capable of bonding to copper as indicated such as water, alcohols, amines, ethers, sulfoxides, and other solvents and competing ligands). When L is present, the copper complex of the carboxylic acid can exist in either the binuclear configuration of Structure X or the mononuclear configuration of Structure X-A depending on the affinity of L for copper. It should be recalled from the section on copper complexes of acylsalicylates, supra, that these compounds are also carboxylic acids that complex with copper in the nonsolvated state to form a binuclear coordination compound and, when in the solvated state, complex with copper in either the binuclear or mononuclear configurations shown by Structures I and II, respectively. Similarly, fatty acids, which include saturated and unsaturated monocarboxylic acids of up to about $C_{19}$ in length, can complex in either the binuclear or mononuclear configurations in their solvated states.

Structure X     Structure X-A

Copper acetate, $Cu(II)_2(acetate)_4$, a binuclear copper complex of a $C_2$, straight chain, aliphatic carboxylic acid, was evaluated for anticonvulsant activity in a test in which aspirin (not complexed with copper) was also evaluated. It is known that in high doses aspirin (and other salicylates) have toxic effects on the central nervous system, including convulsions [Goodman and Gilman (Eds.), *The Pharmacological Basis of Therapeutics* (1980), 6th ed., MacMillan, New York, p. 689].

As shown in Table VI, aspirin was found to be inactive at 30, 100, 300 and 600 mg/kg in both seizure models at both time intervals, 30 minutes and 4 hours. Because it was thought that a copper-containing compound injected subcutaneously at the same site as the site of subcutaneous Metrazol injection might somehow, through a direct interaction with Metrazol perhaps, prevent the induction of seizures with Metrazol, and as a result cause an apparent anticonvulsant effect, this aspect of administration was investigated.

TABLE VI

ANTICONVULSANT ACTIVITY OF ASPIRIN AND COPPER ACETATE

| | | Seizure Model | |
|---|---|---|---|
| Compound | Route | Maximal Electroshock | Metrazol |
| Aspirin | IP | I[1] | I[1] |
| $Cu(II)_2(acetate)_4$ | SC* | I[1] | A at 30, 100, 300 and 600 mg/kg at 30 min. and 4 hrs. |
| $Cu(II)(Metrazol)Cl_2$ | IP | I | A at 30 mg/kg at 30 min. |
| | SC | I | A at 300 mg/kg at 4 hrs. |
| $Cu(II)_2(acetate)_4$ | SC | NT | I[1] |
| $Cu(II)_2(acetate)_4$ | IP | I[1,2,3] | A at 30 mg/kg at 30 min.[4,3] |
| $Cu(II)_2(acetate)_4$ | IP | NT | A at 10 and 20 mg/kg at 30 min. and A at 5, 10 and 20 mg/kg at 4 hrs. |
| $Cu(II)_2(acetate)_4$ | IG | I[1] | I[1] |

A = Active; NT = Not Tested.
IP = Intraperitoneal.
SC = Subcutaneous at site different from injection of Metrazol.
IG = Intragastric.
*Same injection site used for injection of Metrazol.
[1]Inactive 30, 100, 300 and 600 mg/kg at 30 min. and 4 hrs.
[2]Rotating rod toxicity at 30, 100, 300 and 600 mg/kg.
[3]Lethal at 30, 100, 300 and 600 mg/kg at 4 hrs.
[4]Lethal at 100, 300 and 600 mg/kg at 30 min.

As shown in Table VI, $Cu(II)_2(acetate)_4$ was active when injected at the same site as the site of Metrazol injection and the copper complex of Metrazol, Cu(II)(Metrazol)(Cl$_2$), had some anticonvulsant activity when injected at a site different from the site of Metrazol injection. In addition, the Metrazol complex produced no rotating rod toxicity at doses up to 600 mg/kg, which is remarkable since Metrazol is a potent central nervous system stimulant accounting for its seizure producing capacity. Such stimulation produces marked rotating rod toxicity.

The lack of anticonvulsant activity of $Cu(II)_2$-(acetate)$_4$ when it is given subcutaneously at an alternate site of injection is consistent with the lack of anticonvulsant effect following subcutaneous injection of either copper acetate or copper chloride at a site different from the site of Metrazol injection as reported previously [Sorenson et al., *Anticonvulsant Activity of Some Copper Complexes, In: Trace Substances in Environmental Health-XIII*, D. D. Hemphill, ed., University of Missouri Press, Columbia, Mo., pp. 360–367 (1979); U.S. patent application Ser. No. 344,309 filed Feb. 1, 1982]. There it was reported that no anticonvulsant activity was found with either copper acetate or copper chloride using doses of 50, 100 and 300 mg/kg at 0.75, 1.5 and 3 hours post subcutaneous injection at a site different from the site of Metrazol injection.

On the other hand, the observation of anticonvulsant activity at a very low dose, 5 mg/kg, following intraperitoneal administration of $Cu(II)_2(acetate)_4$ at a site different from the subcutaneous administration of Metrazol, suggests that copper acetate is effective in inhibiting Metrazol-induced seizures by some mechanism other than a direct interaction with Metrazol when the rate of absorption and the amount of compound absorbed from the site of administration is increased, as it is with intraperitoneal administration. Consistently, copper acetate was found to be inactive when administered orally, the route which is likely to provide the slowest rate of absorption and the smallest amount of compound absorbed, in comparison with the subcutaneous and intraperitoneal routes of administration. It may, however, be that a method of oral dosing can be developed to produce anticonvulsant activity following oral treatment with copper complexes using prolonged treatment or facilitating oral absorption.

Other copper complexes of carboxylic acids which have been tested for anticonvulsant activity are the following: (1) $Cu(II)_2(valproate)_4$, also known as $Cu(II)_2(dipropylacetate)_4$, which is the binuclear copper complex of valproic acid, a known anticonvulsant drug (valproic acid is a $C_7$, branched chain, aliphatic carboxylic acid); (2) $Cu(II)_2(phenylacetate)_4$, a binuclear copper complex of an aliphatic carboxylic acid; and (3) $Cu(II)_2(benzoate)_4$, a binuclear copper complex of an aryl or aromatic carboxylic acid. The data obtained with these compounds are presented in Table VII. $Cu(II)_2(valproate)_4$ and $Cu(II)_2(phenylacetate)_4$ were effective in protecting against Metrazol-induced seizures while $Cu(II)_2(benzoate)_4$ was effective in protecting against both Maximal Electroshock and Metrazol-induced seizures.

TABLE VII

ANTICONVULSANT ACTIVITY OF COPPER COMPLEXES OF CARBOXYLIC ACIDS

| | | Seizure Model | |
|---|---|---|---|
| Complex | Route | Maximal Electroshock | Metrazol |
| $Cu(II)_2$ (valproate)$_4$ | IP | I | A at 100 mg/kg at 30 min. |
| | SC | I | A at 600 mg/kg at 4 hr. |
| $Cu(II)_2$ (phenylacetate)$_4$ | IP | I | A at 300 mg/kg at 4 hr.[1] |
| $Cu(II)_2$ (benzoate)$_4$ | IP | A at 300 mg/kg at 30 min.[1] | A at 30, 100[1] and 300[1] mg/kg at 30 min. |

[1]Rotating rod toxicity at 300 mg/kg.

COPPER COMPLEXES OF KNOWN ANTICONVULSANT AND ANTIEPILEPTIC DRUGS

Numerous compounds are known to have anticonvulsant and antiepileptic activity. Some of the better known therapeutic agents, listed in Table VIII, fall into the following classes: hydantoins, barbiturates, desoxybarbiturates, iminostilbenes, acetylureas, succinimides, benzodiazepines, oxazolidinediones, sulfonamides and fatty acids. [See K. W. Leal and A. S. Troupin, *Clinical Pharmacology of Anti-epileptic Drugs: A Summary of*

*Current Information,* Clin. Chem. 23: 1964–1968 (1977), hereby incorporated by reference.] Copper complexes of the foregoing anticonvulsant and antiepileptic drugs can be used in the practice of the present invention.

TABLE VIII
KNOWN ANTICONVULSANT AND ANTIEPILEPTIC DRUGS

| Class | Example |
|---|---|
| Hydantoins | Phenytoin (Dilantin) |
|  | Desmethylmephenytoin |
|  | Desethylethotoin |
|  | 5-Ethyl-5-phenylhydantoin |
| Barbiturates | Phenobarbital |
|  | Mephobarbital |
|  | Metharbital |
| Thiobarbiturates | Thiopental |
| Desoxybarbiturates | Primidone |
| Iminostilbenes | Carbamazepine |
| Acetylureas | Phenacemide |
| Succinimides | Desmethylmethsuximide |
|  | Ethosuximide |
|  | Desmethylphensuximide |
|  | α-Methyl-α-phenylsuccinimide |
| Benzodiazepines | Chlorazepam |
|  | Desmethyldiazepam |
|  | Diazepam |
|  | Chlorazepate |
|  | Chlordiazepoxide |
|  | Oxazepam |
| Oxazolidinediones | Desmethyltrimethadione |
|  | Desmethylparamethadione |
| Sulfonamides | Acetazolamide |
| Fatty Acids | Sodium Valproate |

The general structure of hydantoins, barbiturates and thiobarbiturates is depicted schematically by Structure XI.

Structure XI

For hydantoins, X represents —NH—, R and R' are branched or unbranched lower alkyl groups, aryl groups or branched or unbranched lower alkyl or aryl groups, which may be substituted with halogen or oxygen-containing (e.g., hydroxy or alkoxy) and nitrogen-containing (e.g., amino or nitro) substituents. L represents solvating or other ligands capable of bonding with copper as indicated such as water, alcohols, amines, ethers, sulfoxides and other solvents and competing ligands.

For barbiturates, X represents and R, R' and L are as described for hydantoins.

For thiobarbiturates, sulfur replaces oxygen in bonding to copper as illustrated for barbiturates.

For oxazolidinediones, X represents —O— and R, R' and L are as described for hydantoins.

For succinimides, X represents —CH$_2$— and R, R' and L are as described for hydantoins.

For acetylureas, X represents NH$_2$ and is not bonded to carbon-5 to give an acyclic ligand. R, R' and L are as described for hydantoins.

For desoxybarbiturates the general structure is

Structure XII and R, R' and L are as described for hydantoins.

For iminostilbenes the general structures may be

Structure XIII or

Structure XIV where R and R' are the same or as described for hydantoins and L is as described for hydantoins.

For benzodiazepines the general structure may be

Structure XV or

-continued

Structure XVI where R and R' are hydrogen, halogen or nitro substituents, R" is hydrogen, alkyl, or the amide group is replaced by a group yielding an amide group on hydrolysis in vivo, and L is as described for hydantoins. The bonding atom in Structure XV may be replaced with N-oxide, In Structure XVI, X may be an oxygen of an N-oxide. The C-3 carbon may also be substituted with a carboxyl or hydroxyl group.

For Sulfonamides, the general structure is

Structure XVII where R represents aryl, alkyl-aryl, a heterocycle or substituted aryl, alkyl-aryl or heterocycle wherein the substituents are halogen or oxygen-containing (e.g., hydroxy or alkoxy) or nitrogen-containing (e.g. amino or nitro) substituents. R' may be H or the same as R. L is as described for hydantoins.

With the hypothesis that copper complexes of the antiepileptic drugs might be the active metabolites of these drugs, several copper complexes of known antiepileptic drugs were synthesized and tested for their anticonvulsant activity. The first series of tests were performed with the copper complex of amobarbital and the results indicated that the copper complex of this known anticonvulant drug was a more potent anticonvulsant than sodium (Na) amobarbital. The data are presented in Table IX.

TABLE IX

COMPARISON OF THE SODIUM AND COPPER AMOBARBITAL ANTICONVULSANT IN THE MAXIMAL ELECTROSHOCK SEIZURE MODEL FOLLOWING INTRAPERITONEAL INJECTION

| Compound | Number of Animals Treated | Dose in mg/kg | Average Sleep Time, minutes | Protection[1] Against Seizure |
|---|---|---|---|---|
| Na amobarbital | 5 | 65 | 0 | 0 |
| Cu(II)(amobarbital)$_2$ | 5 | 65 | 16[2] | 100 |

[1]Percent protected.
[2]All animals slept.

Subsequently, the anticonvulsant activity of copper complexes of dilantin, valproate, phenobarbital (and pyridine and imidazole solvates thereof), amobarbital, lorazepam, α-methyl-α-phenylsuccinimide, carbamazepine, clonazepam, oxazepam, 5-ethyl-5-phenylhydantoin, thiopental and diazepam was investigated in Phase I testing, and for those compounds found to be active, Phase II testing. The results are presented in Table X.

TABLE X

PHASE I AND SOME PHASE II ANTICONVULSANT DATA FOR COPPER COMPLEXES OF ANTIEPILEPTIC DRUGS

| Compound | Route[2] | Challenge Time | Seizure Model[1] MES | Metrazol |
|---|---|---|---|---|
| Cu(II)(Dilantin)$_2$(H$_2$O)$_3$ | IP | 30 min | 30 | 100 |
|  |  | 4 hrs | 30 | 100 |
| Cu(II)(Dilantin)$_2$(H$_2$O)$_3$ | IP[3] | 4 hrs[4] | 13 | NT[5] |
| Dilantin | IP[3] | 1 hr[4] | 7 | Potentiates Metrazol seizures |
| Cu(II)$_2$(Valproate)$_4$ | IP | 30 min | I | 100 |
|  |  | 4 hrs | I | I |
| Cu(II)$_2$(Valproate)$_4$ | SC | 30 min | I | I |
|  |  | 4 hrs | I | 600 |
| Valproic Acid | IP[3] | 15 min[4] | 272 | 149 |
| Cu(II)(Phenobarbital)$_2$(H$_2$O)$_{5.5}$ | IP | 30 min | 30 | 5 |
|  |  | 4 hrs | 30 | 5 |
| Cu(II)(Phenobarbital)$_2$(H$_2$O)$_{5.5}$ | SC | 30 min | 30 | 30 |
|  |  | 4 hrs | 30 | 30 |
| Cu(II)(Phenobarbital)$_2$(H$_2$O)$_3$ | IP | 30 min | 30 | 5 |
|  |  | 4 hrs | 30 | 5 |
| Cu(II)(Phenobarbital)$_2$(H$_2$O)$_3$ | SC | 30 min | 30 | 30 |
|  |  | 4 hrs | 30 | 30 |
| Cu(II)(Phenobarbital)$_2$(H$_2$O)$_3$ | IP[3] | 2 hrs[4] | 16 | 10 |
| Cu(II)$_n$(Phenobarbital)$_n$(H$_2$O)$_{2n}$(H$_2$O)$_{3n}$ | SC | 30 min | 100 | 30 |
|  |  | 4 hrs | 30 | 30 |
| Phenobarbital | IP[3] | 1 hr[4] | 22 | 13 |
| Cu(II)(Phenobarbital)$_2$(pyridine)$_2$ | IP | 30 min | 100 | 30 |
|  |  | 4 hrs | 100 | 30 |
| Cu(II)(Phenobarbital)$_2$(pyridine)$_2$ | SC | 30 min | I | I |
|  |  | 4 hrs | 30 | 30 |
| Cu(II)(Phenobarbital)$_2$(pyridine)$_2$ | IP[3] | 2 hrs[4] | 17 | 9 |
| Cu(II)$_n$(Phenobarbital)$_n$(pyridine)2n(H$_2$O)$_{3n}$ | SC | 30 min | 100 | 30 |
|  |  | 4 hrs | 30 | 30 |
| Cu(II)$_n$(Phenobarbital)$_n$(pyridine)$_{2n}$(H$_2$O)$_{3n}$ | SC | 30 min | 30 | 30 |
|  |  | 4 hrs | 100 | 30 |
| Cu(II)(Phenobarbital)$_2$(imidazole)$_2$ | IP | 30 min | 100 | 300 |
|  |  | 4 hrs | 100 | 30 |
| Cu(II)(Phenobarbital)$_2$(imidazole)$_2$ | SC | 30 min | I | 100 |
|  |  | 4 hrs | 100 | 100 |
| Na$_2$[Cu(II)(Phenobarbital)$_4$](H$_2$O)$_2$ | IP | 30 min | 30 | 30 |
|  |  | 4 hrs | 100 | 100 |
| Na$_2$[Cu(II)(Phenobarbital)$_4$](H$_2$O)$_2$ | SC | 30 min | 30 | 30 |
|  |  | 4 hrs | 30 | 100 |
| Na$_2$[Cu(II)(Phenobarbital)$_4$](H$_2$O)$_2$ | IP[3] | 6 hrs[4] | 25 | 20 |
| Cu(II)(Amobarbital)$_2$(H$_2$O)$_{2.5}$ | IP | 30 min | 300 | 30 |
|  |  | 4 hrs | I | I |
| Cu(II)(Amobarbital)$_2$(H$_2$O)$_2$ | IP | 30 min | 100 | 100 |
|  |  | 4 hrs | I | I |
| Cu(II)(Amobarbital)$_2$ | SC | 30 min | 300 | 100 |

TABLE X-continued
PHASE I AND SOME PHASE II ANTICONVULSANT DATA FOR COPPER COMPLEXES OF ANTIEPILEPTIC DRUGS

| Compound | Route[2] | Challenge Time | Seizure Model[1] MES | Metrazol |
|---|---|---|---|---|
| (H$_2$O)$_2$ | | 4 hrs | I | I |
| Cu(II)(Amobarbital)$_2$ | IP[3] | 30 min[4] | 87 | 87 |
| (H$_2$O)$_{2.5}$ | | | | |
| Amobarbital | IP | 30 min | 30 | 100 |
| | | 4 hrs | I | I |
| Amobarbital | IP[3] | 15 min[4] | 45 | 53 |
| Cu(II)(Amobarbital)$_2$ | IP | 30 min | 300 | 100 |
| (pyridine)$_2$ | | 4 hrs | 300 | 30 |
| Cu(II)(Amobarbital)$_2$ | SC | 30 min | I | 600 |
| (pyridine)$_2$ | | 4 hrs | 100 | 600 |
| Cu(II)(Amobarbital)$_2$ | IP | 30 min | 600 | 300 |
| (imidazole)$_2$ | | 4 hrs | I | I |
| Cu(II)(Amobarbital)$_2$ | SC | 30 min | I | I |
| (imidazole)$_2$ | | 4 hrs | I | 600 |
| Cu(II)(Lorazepam)$_2$ | IP | 30 min | 20 | I |
| (Cl)$_2$H$_2$O | | 4 hrs | 30 | I |
| Cu(II)(Lorazepam)$_2$ | SC | 30 min | 20 | I |
| (Cl)$_2$H$_2$O | | 4 hrs | 100 | I |
| Lorazepam | IP[3] | 1 hr[4] | 24 | 0.02 |
| Cu(II)(Diazepam)$_2$(Cl)$_2$ | IP | 30 min | 30 | 30 |
| | | 4 hrs | 30 | 30 |
| Diazepam | IP[3] | 1 hr[4] | 19 | 0.17 |
| Cu(II)α-methyl-α-phenyl-succinimide(H$_2$O)$_{0.75}$ | IP | 30 min | 100 | 100 |
| | | 4 hrs | I | 100 |
| Cu(II)α-methyl-α-phenyl-succinimide(H$_2$O)$_{0.75}$ | SC | 30 min | 30 | 30 |
| | | 4 hrs | 100 | 600 |
| Cu(II)Carbamazepine(H$_2$O)$_2$ | IP | 30 min | 10 | 30 |
| | | 4 hrs | 100 | I |
| Cu(II)Carbamazepine(H$_2$O)$_2$ | SC | 30 min | 30 | 300 |
| | | 4 hrs | 100 | 300 |
| Carbamazepine | IP[3] | — | 9 | Potentiates Metrazol seizures |
| Cu(II)(Clonazepam)$_2$(Cl)$_2$ | IP | 30 min | 10 | 1 |
| | | 4 hrs | I | 1 |
| Cu(II)(Clonazepam)$_2$(Cl)$_2$ | SC | 30 min | 1 | 1 |
| | | 4 hrs | 30 | 1 |
| Cu(II)(Clonazepam)$_2$(Cl)$_2$ | IP[3] | 30 min[4] | 25 | 0.05 |
| | | | (30 min)[4] | 1 |
| Clonazepam | IP[3] | — | 19 | 0.2 |
| Cu(II)oxazepam | IP | 30 min | 10 | 1 |
| | | 4 hrs | I | 10 |
| Cu(II)5-ethyl-5-phenyl-hydantoin(H$_2$O)$_{2.5}$ | IP | 30 min | 100 | 300 |
| | | 4 hrs | 100 | 100 |
| Cu(II)5-ethyl-5-phenyl-hydantoin(H$_2$O)$_{2.5}$ | SC | 30 min | 100 | 30 |
| | | 4 hrs | 30 | 100 |
| Cu(II)5-ethyl-5-phenyl-hydantoin(CH$_3$OH) | IP | 30 min | 100 | 100 |
| | | 4 hrs | 100 | I |
| Cu(II)5-ethyl-5-phenyl-hydantoin(CH$_3$OH) | SC | 30 min | 100 | 100 |
| | | 4 hrs | 30 | 300 |
| Cu(II)5-ethyl-5-phenyl-hydantoin(HO)(Cl)(CH$_3$OH) | IP | 30 min | 30 | 30 |
| | | 4 hrs | I | I |
| Cu(II)(N—thiopental)$_2$(H$_2$O)$_{2.5}$ | IP | 30 min | I | I |
| | | 4 hrs | I | I |
| Cu(II)(N—thiopental)$_2$(H$_2$O)$_{2.5}$ | SC | 30 min | I | I |
| | | 4 hrs | I | 30 |
| Cu(II)(S—thiopental)$_2$(H$_2$O)$_2$ | IP | 30 min | I | I |
| | | 4 hrs | I | I |
| Cu(II)(S—thiopental)$_2$(H$_2$O)$_2$ | SC | 30 min | I | I |
| | | 4 hrs | I | I |

[1] The numerical values are the lowest doses in milligrams per kilogram of body weight, I = inactive, MES = maximal electroshock.
[2] IP = intraperitoneal, SC = subcutaneous.
[3] Phase II data.
[4] Time of peak activity in Phase II studies and ED$_{50}$ values for inhibition of seizures.
[5] Clonic seizures inhibited but animals stimulated by Metrazol (continuous running).

The data provided in Table X for the inhibition of Maximal electroshock and Metrazol-induced seizures are the lowest effective doses (mg/kg). If a compound is found to be effective and nontoxic in Phase I evaluations, which are done to detect anticonvulsant activity, it is further examined in Phase II studies to determine time of peak effect and ED$_{50}$. Since Phase II evaluations are done only after Phase I, there are Phase II data for a smaller number of compounds. There are no Phase I data for the known anticonvulsant drugs since the NINCDS had no need to attempt to detect anticonvulsant activity for these established anticonvulsant agents. Phase II-ED$_{50}$ data for some of the compounds are included in Table X. Table X also contains Phase II time of peak effect data for the parent anticonvulsant drugs.

The copper complex of dilantin was found to have a rapid onset and prolonged duration in inhibiting only Maximal Electroshock-induced seizures. Dilantin is also known to only inhibit Maximal Electroshock-induced seizures but it potentiates Metrazol-induced seizures. The copper complex did not potentiate but did block both types of seizures. Phase II data for Cu(II)(dilantin)$_2$ indicate that it has a time of peak effect of 4 hours, which is longer than the time of peak effect for dilantin (1 hour).

In Phase I studies, Cu(II)$_2$(valproate)$_4$ appeared to be ineffective against Maximal Electroshock seizures, but had some inhibitory activity against Metrazol-induced seizures. This compound had a rapid onset and short duration of activity following intraperitoneal administration and, consistently, a prolonged onset of activity at a higher dose following subcutaneous administration. The parent compound (valproic acid) was also weakly effective against Maximal Electroshock-induced seizures and more effective against Metrazol-induced seizures.

With few exceptions the phenobarbital complexes were also found to have rapid onset and prolonged durations of activity in both models of seizure. Although the data do not allow a rigorous comparison of these compounds, it is of interest that the pyridine and imidazole complexes were somewhat less effective than the aquo complexes. All three solvates had prolonged onsets of action following subcutaneous administration. The aquo phenobarbital complexes were most effective regardless of the route of administration and recent data show that the tri- and penta-aquo complexes are effective in preventing the Metrazol-induced seizure at a dose much lower than the lowest dose routinely used as the lowest dose in Phase I studies, 30 mg/kg. Activity at 5 mg/kg would appear to indicate greater activity than phenobarbital which has an ED$_{50}$ of 13 mg/kg.

Copper (II)(amobarbital)$_2$ complexes also appear to have rapid onsets and short durations of activity following intraperitoneal administration, which appears to be reversed with subcutaneous administration.

The copper complex of lorazepam appears to have a rapid onset of action and prolonged duration following intraperitoneal and subcutaneous administration. This complex appears to be quite active. However, this complex involves complexation at the 4-nitrogen and its stability may not be as high as others. The copper complex of diazepam also appears to have a rapid onset of action and prolonged duration following intraperitoneal administration.

Cu(II)α-methyl-α-phenylsuccinimide and Cu(II)5-ethyl-5-phenylhydantoin complexes were also effective in preventing both types of seizure with rapid onsets of action and prolonged durations of action following subcutaneous and intraperitoneal administration.

Cu(II)oxazepam also protected against both types of seizure and seems to be more prolonged in its action against Metrazol induced seizures.

The Cu(II)carbamazepine complex was also an effective anticonvulsant. However, it did not potentiate Metrazol seizures while the parent drug is known to be a seizure-inducing agent.

$Cu(II)(clonazepam)_2$ was found to be a very potent anticonvulsant. Doses less than those used in routine Phase I studies were required to obtain the lowest effective doses in both models of seizure. In addition, the results of Phase II studies with this complex show that the complex is four times as effective as the parent drug.

The copper complexes of thiopental were tested at lower doses than usually used in Phase I studies. It is anticipated that higher doses of these complexes will evidence anticonvulsant activity.

Since all of the foregoing drugs (parent compounds or ligands) are known to be active anticonvulsants, simultaneous comparisons of the ligands and their copper complexes are ultimately required to determine whether or not these complexes are more active than the ligands, as suggested by some of the data. Nevertheless, the data in Table X do indicate that all the copper complexes tested have anticonvulsant activity. Even if some of the copper complexes are not more active than the parent compound, they may nonetheless prove useful in therapy regimens alone or in conjunction with other complexes, especially if their time of peak effect differs from that of the parent and also especially if the copper complexes are less toxic and associated with fewer side effects than the parent compounds.

The foregoing experiments with copper complexes of acylsalicylates, salicylates, amino acids, imines, carboxylic acids and known anticonvulsant and antiepileptic drugs demonstrate that such complexes have anticonvulsant activity. That the intact copper complex may play a key role in the observed anticonvulsant activity is consistent with the observation that inorganic copper salts, which contain much more copper on a weight percentage basis, do not have anticonvulsant activity, or have less anticonvulsant activity based upon copper content, and also with the observation that there is a lack of an apparent direct correlation between the observed anticonvulsant activity of copper complexes and the amount of copper in them.

The organic compounds of copper or their solvates and other chemical modifications useful in the present invention can be administered as solid, solution, suspension, or ointment-dosing formulations in a concentration range of between about 0.01 to about 600 mg/kg of body weight and preferably between about 0.01 to about 100 mg/kg of body weight. The compounds can be administered orally, topically or parenterally, that is, intraperitoneally, subcutaneously or intravenously.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

I claim:

1. A method of treating convulsive tremors or convulsive seizures comprising administration to a mammal of a therapeutically effective amount of an organic compound of copper having anticonvulsant activity selected from the group consisting of a copper complex of an amino acid and a mixture of copper complexes of amino acids.

2. A method of treating epilepsy comprising administration to a mammal of a therapeutically effective amount of an organic compound of copper having antiepileptic activity selected from the group consisting of a copper complex of an amino acid and a mixture of copper complexes or amino acids.

3. The method according to claim 1 or 2 wherein the organic compound of copper is selected from the group consisting of:
   (a) Cu(II)(L-threoninate)(L-serinate);
   (b) Cu(II)(L-threoninate)(L-alaninate);
   (c) $Cu(II)(L-valinate)_2H_2O$;
   (d) $Cu(II)(L-threoninate)_2H_2O$;
   (e) $Cu(II)(L-alaninate)_2$;
   (f) $Cu(II)(L-phenylalaninate)_2$;
   (g) $Cu(II)(L-cystinate)_2H_2O$;
   (h) $Cu(II)(L-isoleucinate)_2$;
   (i) $Cu(II)(L-glutamate)_2$;
   (j) $Cu(II)(L-tryptophanate)_2$;
   (k) $Cu(II)(L-serinate)_2$; and
   (l) $Cu(II)(L-leucinate)_2$.

4. A method of treating convulsive tremors or convulsive seizures comprising administration to a mammal of a therapeutically effective amount of an organic compound of copper having anticonvulsant activity selected from the group consisting of a copper complex of an imine and a mixture of copper complexes of imines.

5. A method of treating epilepsy comprising administration to a mammal of a therapeutically effective amount of an organic compound of copper having antiepileptic activity selected from the group consisting of a copper complex of an imine and a mixture of copper complexes of imines.

6. The method according to claim 4 or 5 wherein the imine is a bisethyleneimine Schiff base.

7. The method according to claim 6 wherein the bisethyleneimine Schiff base is selected from the group consisting of:
   (a) Cu(II)bisacetylacetonethyleneimine; and
   (b) Cu(II)bissalicylatoethyleneimine.

8. The method according to claim 4 or 5 wherein the imine is a salicylidene-amino acid Schiff base.

9. The method according to claim 8 wherein the salicylidene-amino acid Schiff base is selected from the group consisting of:
   (a) Cu(II)salicylidene-L-valinate; and
   (b) Cu(II)salicylidene-L-histidinate.

10. The method according to claim 4 or 5 wherein the imine is a pyridoxylidene-amino acid Schiff base.

11. The method according to claim 10 wherein the pyridoxylidene-amino acid Schiff base is selected from the group consisting of:
    (a) $Cu(II)pyridoxylideneglycinate(H_2O)_{1.5}$;
    (b) $Cu(II)pyridoxylidene-L-serinate(H_2O)$;
    (c) $Cu(II)pyridoxylidene-L-tryptophanate(H_2O)_2$; and
    (d) $Cu(II)pyridoxylidene-L-threoninate(H_2O)_2$.

12. The method according to claim 1, 2, 4 or 5 wherein the organic copper compound is administered intravenously.

13. The method according to claim 1, 2, 4 or 5 wherein the organic copper compounds is administered intraperitoneally.

14. The method according to claim 1, 2, 4 or 5 wherein the organic copper compound is administered subcutaneously.

15. The method according to claim 1, 2, 4 or 5 wherein the organic copper compound is administered orally.

16. The method according to claim 1, 2, 4 or 5 wherein the organic copper compound is administered topically.

17. The method according to claim 1, 2, 4 or 5 wherein the organic copper compound is administered in an amount between about 0.1 to about 100 milligrams per kilogram of body weight.

18. The method according to claim 1 wherein the organic copper compound is administered in an amount between about 0.1 to about 600 milligrams per kilogram of body weight.

19. The method according to claim 1, 2, 4 or 5 wherein the organic copper compound is administered in the form of a solution, suspension or ointment.

20. The method according to claim 19 wherein the solution, suspension or ointment includes saline, ethylene glycol or a suspending agent like polyoxyethylene glycol.

* * * * *